United States Patent
Shmarev et al.

(10) Patent No.: US 9,904,173 B2
(45) Date of Patent: Feb. 27, 2018

(54) METHOD AND APPARATUSES FOR OPTICAL PUPIL SYMMETRIZATION

(71) Applicant: ASML Holding N.V., Veldhoven (NL)

(72) Inventors: Yevgeniy Konstantinovich Shmarev, Lagrangeville, NY (US); Stanislav Smirnov, Danbury, CT (US)

(73) Assignee: ASML Holding N.V., Veldhoven (NL)

( * ) Notice: Subject to any disclaimer, the term of this patent is extended or adjusted under 35 U.S.C. 154(b) by 135 days.

(21) Appl. No.: 14/970,247

(22) Filed: Dec. 15, 2015

(65) Prior Publication Data

US 2016/0209755 A1 Jul. 21, 2016

Related U.S. Application Data

(60) Provisional application No. 62/092,003, filed on Dec. 15, 2014.

(51) Int. Cl.
*G03B 27/72* (2006.01)
*G03F 7/20* (2006.01)
(Continued)

(52) U.S. Cl.
CPC ..... *G03F 7/70133* (2013.01); *G01N 21/4738* (2013.01); *G02B 5/04* (2013.01); *G02B 27/106* (2013.01); *G03F 7/70091* (2013.01); *G03F 7/70191* (2013.01); *G03F 7/70208* (2013.01); *G01N 2201/061* (2013.01); *G01N 2201/068* (2013.01); *G01N 2201/06113* (2013.01)

(58) Field of Classification Search
CPC ............. G03F 7/70091; G03F 7/70133; G03F 7/70191; G03F 7/70208; G01N 21/4738; G01N 2201/061; G01N 2201/06113; G01N 2201/068; G02B 27/106; G02B 5/04

USPC ...................................................... 355/71, 67
See application file for complete search history.

(56) References Cited

U.S. PATENT DOCUMENTS 4,170,401 A 10/1979 Yoder, Jr. et al.
5,016,149 A 5/1991 Tanaka et al.
(Continued)

FOREIGN PATENT DOCUMENTS

TW 201233994 A 8/2012

OTHER PUBLICATIONS

International Search Report directed to App. No. PCT/EP2015/077028, dated Apr. 29, 2016; 2 pages.

*Primary Examiner* — Peter B Kim
(74) *Attorney, Agent, or Firm* — Sterne, Kessler, Goldstein & Fox P.L.L.C

(57) ABSTRACT

An inspection apparatus may determine precise OV measurements of a target on a substrate using an optical pupil symmetrizer to reduce the inspection apparatus's sensitivity to asymmetry and non-uniformity of the illumination beam in the pupil plane. The inspection apparatus includes an illumination system that forms a symmetrical illumination pupil by (1) splitting an illumination beam into sub-beams, (2) directing the sub-beams along different optical branches, (3) inverting or rotating at least one of the sub-beams in two dimensions, and recombining the sub-beams along the illumination path to symmetrize the intensity distribution. The illumination system is further configured such that the first and second sub-beams have an optical path difference that is greater than a temporal coherence length of the at least one beam and less than a depth of focus in the pupil plane of the objective optical system.

30 Claims, 22 Drawing Sheets

(51) Int. Cl.
    *G01N 21/47*     (2006.01)
    *G02B 5/04*     (2006.01)
    *G02B 27/10*     (2006.01)

(56) References Cited

U.S. PATENT DOCUMENTS

| | | |
|---|---|---|
| 2011/0027704 A1 | 2/2011 | Cramer et al. |
| 2012/0013881 A1 | 1/2012 | Den Boef et al. |
| 2012/0033226 A1 | 2/2012 | Manassen et al. |
| 2012/0206703 A1 | 8/2012 | Bhattacharyya et al. |
| 2014/0146297 A1 | 5/2014 | Vainer et al. |

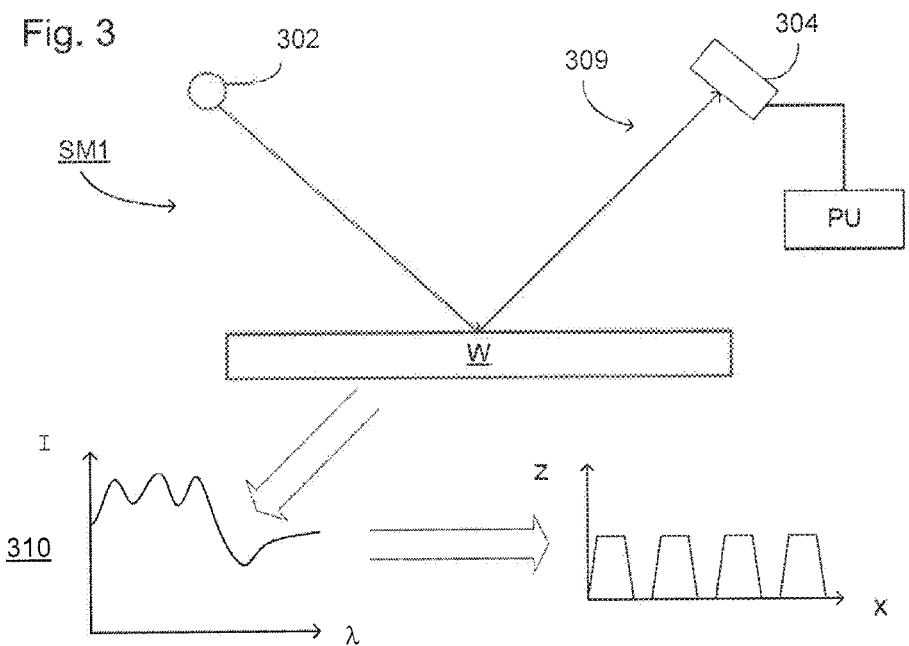
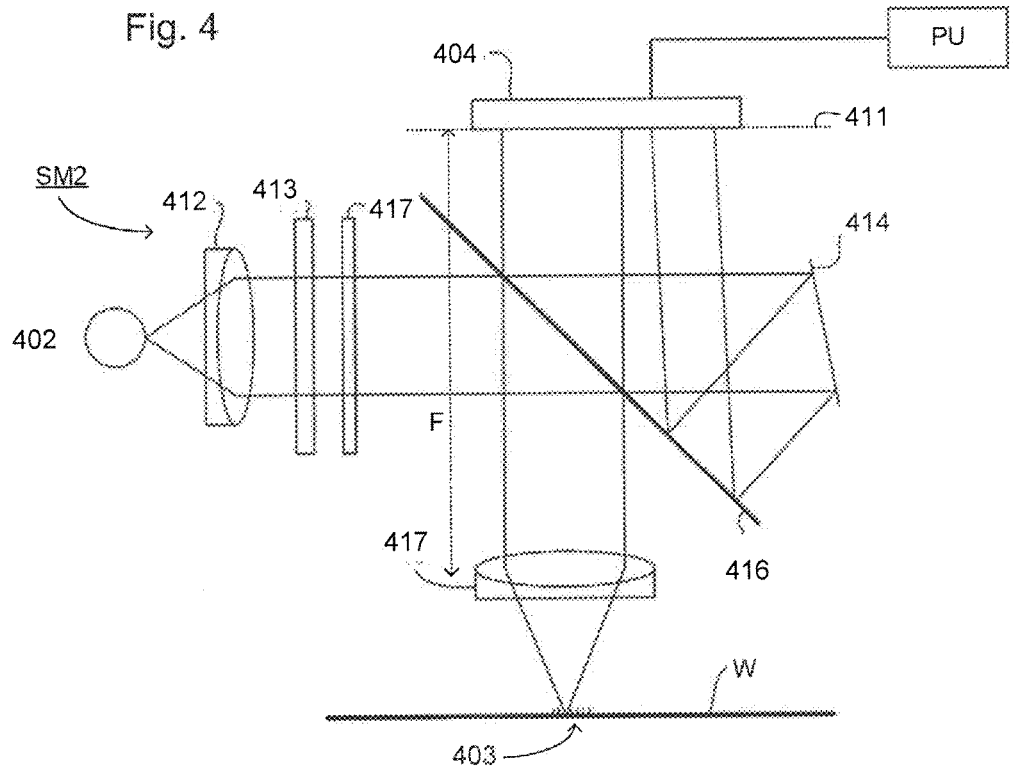

METHOD AND APPARATUSES FOR OPTICAL PUPIL SYMMETRIZATION

This application incorporates by reference in its entirety U.S. provisional application 62/092,003, filed Dec. 15, 2014.

BACKGROUND

Field of the Invention

Embodiments of the present invention relate to a projection system, a lithographic apparatus, a method of projecting a beam of radiation onto a target and a method for manufacturing a device.

Background Art

A lithographic apparatus is a machine that applies a desired pattern onto a substrate, usually onto a target portion of the substrate. A lithographic apparatus may be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti-parallel to this direction. It is also possible to transfer the pattern from the patterning device to the substrate by imprinting the pattern onto the substrate.

In order to monitor the lithographic process, parameters of the patterned substrate are measured. Parameters may include, for example, the overlay error between successive layers formed in or on the patterned substrate and critical linewidth of developed photosensitive resist. This measurement may be performed on a product substrate and/or on a dedicated metrology target. There are various techniques for making measurements of the microscopic structures formed in lithographic processes, including the use of scanning electron microscopes and various specialized tools. A fast and non-invasive form of specialized inspection tool is a scatterometer in which a beam of radiation is directed onto a target on the surface of the substrate and properties of the scattered or reflected beam are measured. By comparing the properties of the beam before and after it has been reflected or scattered by the substrate, the properties of the substrate can be determined. This can be done, for example, by comparing the reflected beam with data stored in a library of known measurements associated with known substrate properties. Spectroscopic scatterometers direct a broadband radiation beam onto the substrate and measure the spectrum (intensity as a function of wavelength) of the radiation scattered into a particular narrow angular range. By contrast, angularly resolved scatterometers use a monochromatic radiation beam and measure the intensity of the scattered radiation as a function of angle.

Such optical scatterometers may be used to measure parameters, such as critical dimensions of developed photosensitive resist or overlay error (OV) between two layers formed in or on the patterned substrate. Properties of the substrate can be determined by comparing the properties of an illumination beam before and after the beam has been reflected or scattered by the substrate. Asymmetries in the shape of a target grating will generally have an impact on the measured overlay. This impact may vary depending on the illumination setting used for the measurement.

A previous technique of OV measurement evaluated difference in intensities of diffraction orders. Such a technique is detailed in US 2012/0013881 A1, which is incorporated by reference in its entirety. A similar technique, disclosed in US 2001/0027704 A1, which is incorporated by reference in its entirety, uses parallel illumination at multiple wavelengths. In both cases, symmetry of the combined illumination beams is important for OV measurement accuracy. The asymmetry of the diffraction orders is a measure of overlay on the target. One problem of these techniques is high sensitivity to non-uniformity and asymmetry of the illumination beam in the pupil plane. Some systems use set of changeable apertures in the pupil plane, but requirements for positioning accuracy of these apertures are extremely tight. New demands for OV accuracy have increased for new generation of lithography metrology tools make this problem extremely important.

SUMMARY

To address the problems described above, an inspection apparatus may determine precise OV measurements of a target on a substrate using an optical pupil symmetrizer (OPS) to reduce the apparatus's sensitivity to asymmetry and non-uniformity of the illumination beam in the pupil plane. The inspection apparatus includes an illumination system providing a plurality of wavelengths of electromagnetic radiation with a more uniform intensity distribution. The OPS forms a symmetrical illumination pupil by (1) splitting an illumination beam into sub-beams and directing the sub-beams along different optical branches, (2) inverting or rotating at least one of the sub-beams in two dimensions, and (3) recombining the sub-beams along the illumination path to symmetrize the intensity distribution. Thus, if, e.g., the initial pupil intensity is defined by function $f(x,y)$ than new one may be $f(x,y)+f(-x,-y)$. This new intensity distribution may be symmetrical so as to automatically compensate any OV error created by any position perturbation of pupil aperture or illumination source.

To minimize interference between the sub-beams, the different optical branches of OPS have an optical path difference that is greater than the temporal coherence length of the illumination beam, but less than the depth of focus in the pupil plane of an objective system of the inspection apparatus. The OPS improves accuracy of the OV measurement without introducing interference between the sub-beams. Such an illumination system may be used with broadband radiation regardless of whether the radiation is polarized or unpolarized. The OPS is less expensive and more robust than previous symmetrization systems, and, as a result, improves OV measurement accuracy with lower volume and cost in comparison to aperture stabilization and tracking by mechatronic techniques.

According to an aspect of the invention, there is provided a device manufacturing method comprising projecting a patterned beam of radiation onto a substrate, using a method of projecting a beam of radiation onto a substrate as disclosed above.

BRIEF DESCRIPTION OF THE DRAWINGS

The accompanying drawings illustrate, but do not limit, the claimed invention. Together with the description, the drawings serve to explain the principles of the claimed invention and to enable a person skilled in the relevant art(s) to make and use the claimed invention.

FIG. 3 depicts aspects of a first scatterometer.

FIG. 4 depicts aspects of a second scatterometer.

Figure 1:
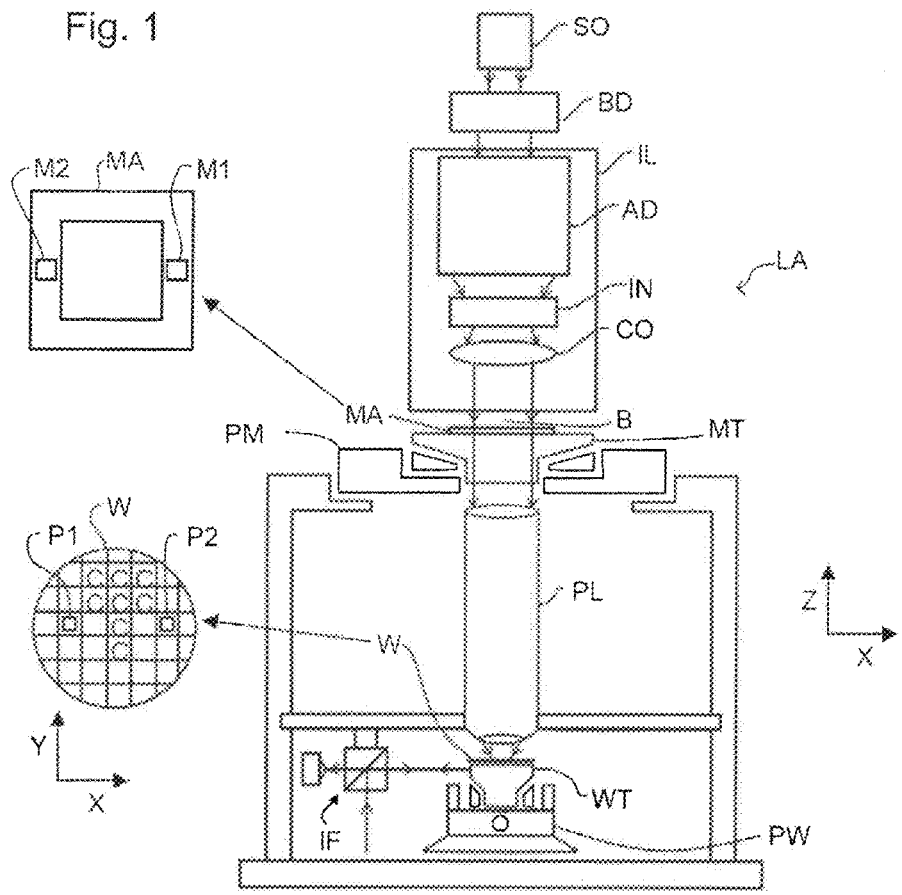
FIG. 1 depicts a lithographic apparatus.

Further features and advantages will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION

This specification discloses one or more embodiments that incorporate features of claimed invention. The disclosed embodiment(s) merely exemplify the claimed invention. The scope of the claimed invention is not limited to the disclosed embodiment(s). The claimed invention is defined solely by the claims appended hereto.

The embodiment(s) described, and references in the specification to "one embodiment," "an embodiment," "an example embodiment," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Before describing such embodiments in more detail, however, it is instructive to present an example environment in which embodiments of the claimed invention may be implemented.

FIG. 1 schematically shows a lithographic apparatus LAP including a source collector module SO according to an embodiment of the present invention. The apparatus comprises an illumination system (illuminator) IL configured to condition a radiation beam B (e.g., EUV radiation); a support structure (e.g., a mask table) MT constructed to support a patterning device (e.g., a mask or a reticle) MA and connected to a first positioner PM configured to accurately position the patterning device; a substrate table (e.g., a wafer table) WT constructed to hold a substrate (e.g., a resist coated wafer) W and connected to a second positioner PW configured to accurately position the substrate; and a projection system (e.g., a reflective projection system) PS configured to project a pattern imparted to the radiation beam B by patterning device MA onto a target portion C (e.g., comprising one or more dies) of the substrate W.

The illumination system may include various types of optical components, such as refractive, reflective, magnetic, electromagnetic, electrostatic or other types of optical components, or any combination thereof, for directing, shaping, or controlling radiation.

The support structure supports, i.e., bears the weight of, the patterning device. It holds the patterning device in a manner that depends on the orientation of the patterning device, the design of the lithographic apparatus, and other conditions, such as for example whether or not the patterning device is held in a vacuum environment. The support structure can use mechanical, vacuum, electrostatic or other clamping techniques to hold the patterning device. The support structure may be a frame or a table, for example, which may be fixed or movable as required. The support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system."

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may be of a type having two (dual stage) or more substrate tables (and/or two or more mask tables). In such "multiple stage" machines the additional tables may be used in parallel, or preparatory steps may be carried out on one or more tables while one or more other tables are being used for exposure.

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD comprising, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may comprise an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may comprise various other components, such as an integrator IN and a condenser CO. The illuminator may be used to condition the radiation beam, to have a desired uniformity and intensity distribution in its cross section.

The radiation beam B is incident on the patterning device (e.g., mask MA), which is held on the support structure (e.g., mask table MT), and is patterned by the patterning device. Having traversed the mask MA, the radiation beam B passes through the projection system PL, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the mask MA with respect to the path of the radiation beam B, e.g., after mechanical retrieval from a mask library, or during a scan. In general, movement of the mask table MT may be realized with the aid of a long-stroke module (coarse positioning) and a short-stroke module (fine positioning), which form part of the first positioner PM. Similarly, movement of the substrate table WT may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

The depicted apparatus could be used in at least one of the following modes:

1. In step mode, the mask table MT and the substrate table WT are kept essentially stationary, while an entire pattern imparted to the radiation beam is projected onto a target portion C at one time (i.e., a single static exposure). The substrate table WT is then shifted in the X and/or Y direction so that a different target portion C can be exposed. In step mode, the maximum size of the exposure field limits the size of the target portion C imaged in a single static exposure.

2. In scan mode, the mask table MT and the substrate table WT are scanned synchronously while a pattern imparted to the radiation beam is projected onto a target portion C (i.e., a single dynamic exposure). The velocity and direction of the substrate table WT relative to the mask table MT may be determined by the (de-)magnification and image reversal characteristics of the projection system PL. In scan mode, the maximum size of the exposure field limits the width (in the non-scanning direction) of the target portion in a single dynamic exposure, whereas the length of the scanning motion determines the height (in the scanning direction) of the target portion.

3. In another mode, the mask table MT is kept essentially stationary holding a programmable patterning device, and the substrate table WT is moved or scanned while a pattern imparted to the radiation beam is projected onto a target portion C. In this mode, generally a pulsed radiation source is employed and the programmable patterning device is updated as required after each movement of the substrate table WT or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Figure 2:
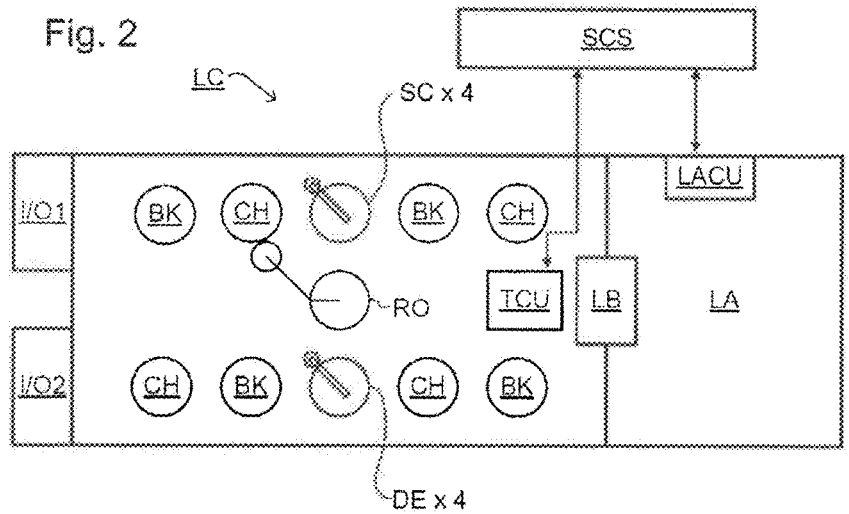
FIG. 2 depicts a lithographic cell or cluster.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. If errors are detected, adjustments may be made to exposures of subsequent substrates, especially if the inspection can be done soon and fast enough that other substrates of the same batch are still to be exposed. Also, already exposed substrates may be stripped and reworked—to improve yield—or discarded, thereby avoiding performing exposures on substrates that are known to be faulty. In a case where only some target portions of a substrate are faulty, further exposures can be performed only on those target portions which are good.

An inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

FIG. 3 depicts a general scatterometer that may be used as an inspection apparatus. The scatterometer comprises broadband (e.g., 400-905 nm) illumination source 302, which projects radiation onto substrate W. The scatterometer further comprises to a spectrometer detector 304, which measures a radiation spectrum 309 (intensity as a function of wavelength) specularly reflected from substrate W. From this data, the structure or profile giving rise to the detected spectrum may be reconstructed by processing unit PU, e.g., by Rigorous Coupled Wave Analysis and non-linear regression or by comparison with a library of simulated spectra as shown at the bottom of FIG. 3. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Another aspect of a scatterometer is depicted in FIG. 4. In this scatterometer, the radiation emitted by broadband illumination source 402 is collimated using collimating lens system 412 and transmitted through filter 413 and polarizer 417, reflected by partially reflected surface 16 and is focused onto substrate W via a microscope objective lens 415, which has a high numerical aperture (NA), preferably at least 0.9 and more preferably at least 0.95. Immersion scatterometers may have lenses with numerical apertures over 1. The reflected radiation passes through partially reflecting surface 416 into a detector 404 in order to have the scatter spectrum detected. Detector 404 may be located in a back-projected pupil plane 411 located is at the focal length of lens system 415. Alternatively, pupil plane 411 may instead be re-imaged with auxiliary optics (not shown) onto detector 404. The pupil plane is the plane in which the radial position of radiation defines the angle of incidence and the angular position defines azimuth angle of the radiation. Detector 404 is preferably a two-dimensional detector so that a two-dimensional angular scatter spectrum of substrate target 403 can be measured. Detector 404 may be, for example, an array of CCD or CMOS sensors, and may use an integration time of, for example, 40 milliseconds per frame. Other appropriate sensors, however, may be used.

A reference beam may be used, for example, to measure the intensity of the incident radiation. To accomplish this, the illumination beam incident on beam splitter 416 part passes through beam splitter 416 as a reference beam towards a reference mirror 414. The reference beam is then projected onto a different part of detector 404 or, alternatively, on to a different detector (not shown).

Filter 413 may comprise a set of interference filters to select a wavelength or waveband of interest, e.g., a 10 nm-wide band, from a spectral range of 400-905 nm. Filter 413 may be tunable rather than comprising a set of different filters. A grating could be used instead of interference filters.

Detector 404 may measure the intensity of scattered light at a single wavelength (or narrow wavelength range), the intensity separately at multiple wavelengths or integrated over a wavelength range. Furthermore, detector 404 may separately measure the intensity of transverse magnetic- and transverse electric-polarized light and/or the phase difference between the transverse magnetic- and transverse electric-polarized light.

Illumination source 402 may be a broadband light source (i.e., one with a wide range of light frequencies or wavelengths—and, therefore, of colors), which gives a large etendue, enabling the mixing of multiple wavelengths. The plurality of wavelengths in the broadband may each have a bandwidth of £ and a spacing of at least 2 £ (i.e., twice the bandwidth). Bandwidth £ may be, for example, 10 nm. Several "sources" of radiation can be different portions of an extended radiation source which have been split using fiber bundles. The fiber bundles are spatially separated but output illumination beams may be directed in parallel through the illumination system. In this way, angle resolved scatter spectra can be measured at multiple wavelengths in parallel. A 3-D spectrum (wavelength and two different angles) may also be measured, which contains more information than a 2-D spectrum. Allowing for more information to be measured increases metrology process robustness. This is described in more detail in EP 1628164 A, which is incorporated by reference herein in its entirety.

Target 403 on substrate W may be a 1-D grating, which is printed such that, after development, the bars are formed of solid resist lines. Target 403 may be a 2-D grating formed of solid resist pillars or vias in the resist. The bars, pillars, or vias may alternatively be etched into the substrate. This pattern is sensitive to chromatic aberrations in projection system PL and illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

Figure 5:
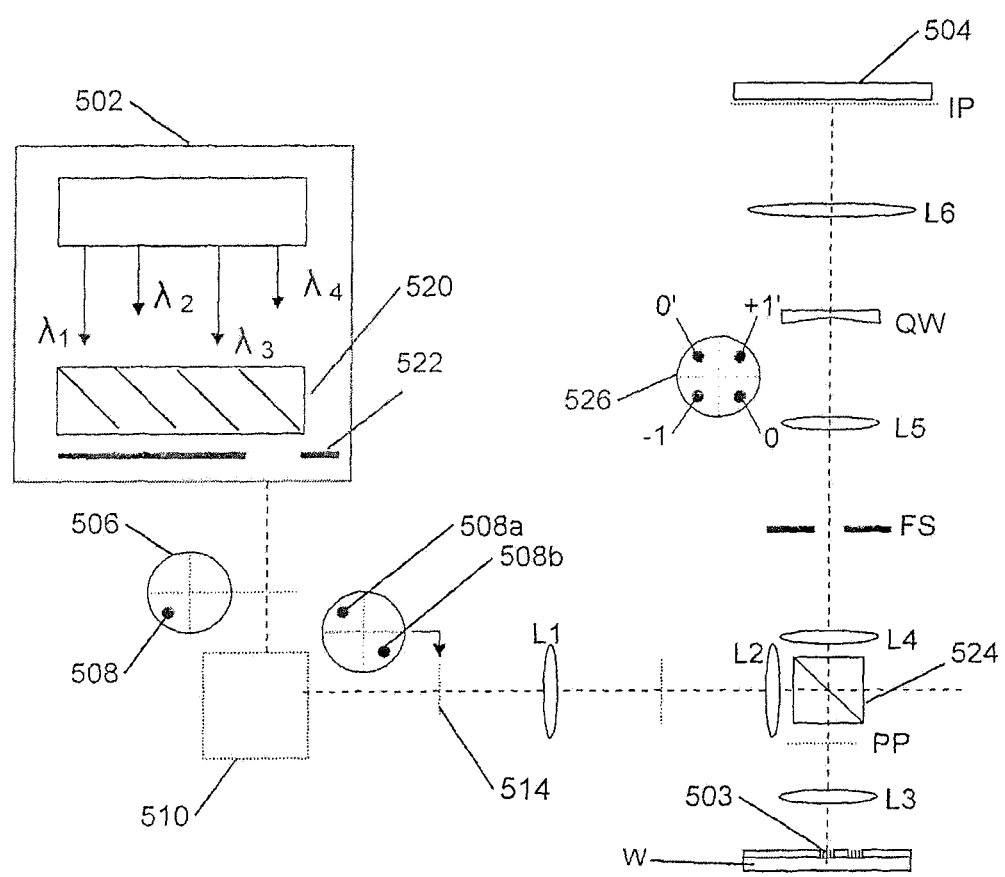
FIG. 5 depicts an inspection apparatus according to one exemplary embodiment.

FIG. 5 illustrates more details of an inspection apparatus that includes an OPS 510. With reference to FIG. 5, a broadband light source 502 provides a plurality of wavelengths of radiation, e.g., wavelengths λ1, λ2, λ3, λ4. In a non-limiting example, plurality of wavelengths λ1, λ2, λ3, λ4 are provided simultaneously, for fast measurement by the apparatus. In another embodiment, a tunable light source provides different wavelengths at different times. The light source 502 may include, for example, a white-light laser or a Xenon lamp that is separated into plurality of wavelengths λ1, λ2, λ3, λ4. A beam directing arrangement 520 may be used to couple light from multiple fibers onto an illumination path. Spatial filter 522 may also be used to limit illumination to a particular quadrant of the illumination path. The illumination pupil 506 at the exit of the illuminator has one illumination beam 508 passing through one quadrant of illumination pupil 506. However, any combination of quadrants may be used simultaneously or sequentially. For example, spatial filter 522 may be configured to block light in at least two of four quadrants of the input pupil aperture of the illumination system.

Figure 6:
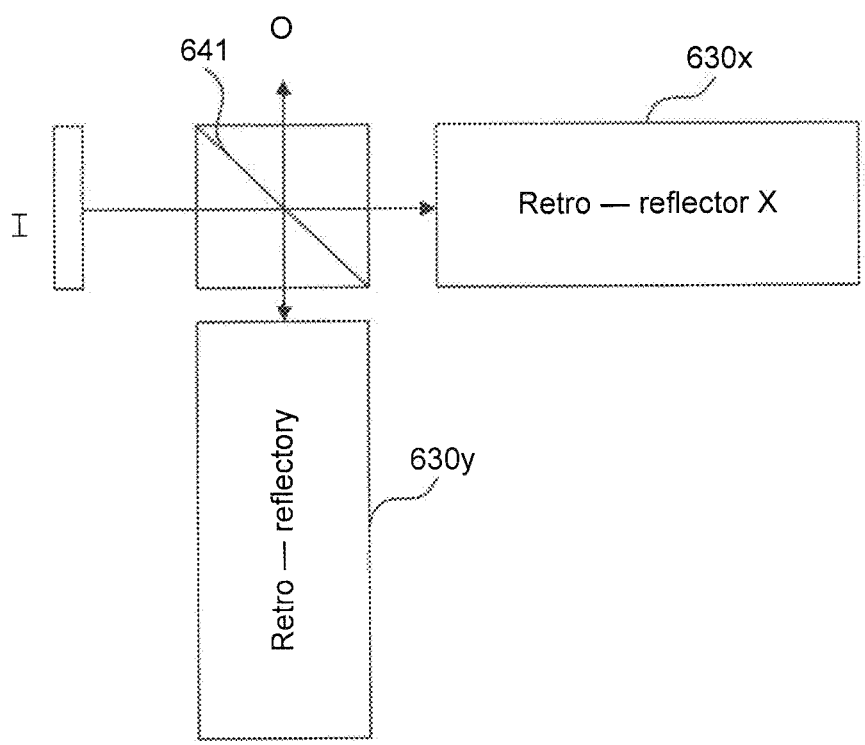
FIG. 6 illustrates a first schematic of an optical pupil symmetrizer with a single beam splitter according to an exemplary embodiment.
Figure 7:
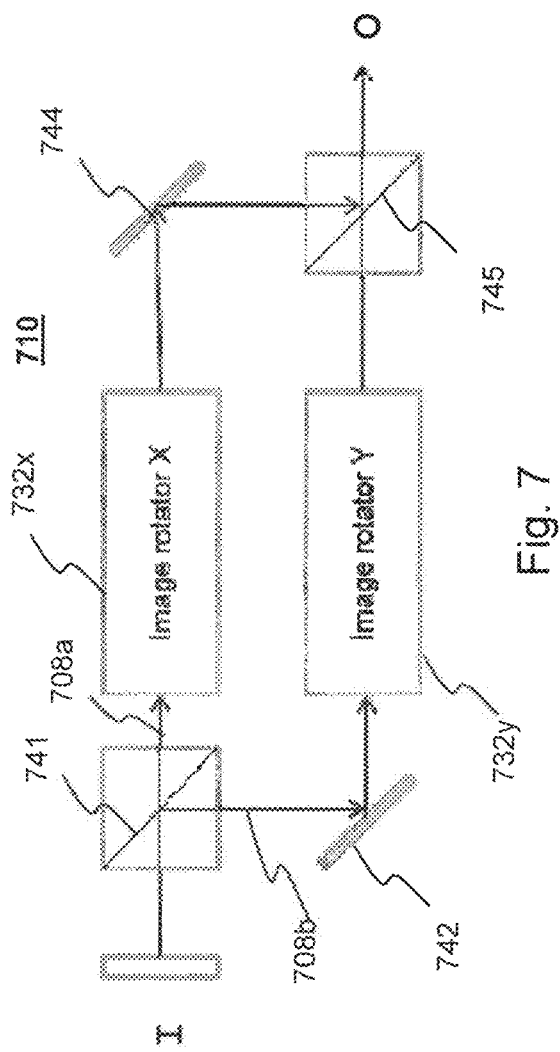
FIG. 7 illustrates a second schematic of an optical pupil symmetrizer with two beam splitters according to an exemplary embodiment.

Illumination beam 508 is sent through OPS 510. OPS 510 splits illumination beam 508 into sub-beams 508a, 508b via a beam splitter. For example, a non-polarizing half-mirror may be used to split 50% of the intensity of illumination beam 508 along a first branch from the other 50% directed along a second branch. OPS 510 forms two sub-beams that are symmetrical about an optical axis. OPS 510 may invert one or both sub-beams 508a, 508b. For example, the prism inverter systems described below may be used to form sub-beams 508a, 508b. FIGS. 6 and 7 illustrate alternative schematic embodiments of the OPS 510. As a result of symmetrical sub-beams 508a, 508b, the illumination pupil plane 514 is now illuminated with two sub-beams 508a, 508b that are mirror images relative to the origin (and have substantially zero spatial frequency).

OPS 510 induces an optical path difference (OPD) between sub-beams 508a, 508b that is greater than the temporal coherence length L of the illumination beam, but less than an depth of focus in the pupil plane of an objective system of the inspection apparatus. The temporal coherence length L may be given by the equation:

$$L = \frac{2\ln(2)}{\pi n} \frac{\lambda^2}{\Delta \lambda},$$

where λ is the wavelength of the illumination, n is the refractive index of the medium, and Δλ is the bandwidth (i.e. spectral width) of the illumination. For example, the OPD may be in the range of 50 μm to 100 μm for a spectral range of 400 nm to 905 nm and a bandwidth of 10 nm. On example is listed in Table 1 below:

TABLE 1

| Wavelength (λ) in μm | .4 | .85 |
|---|---|---|
| Bandwidth (Δλ) in μm | .01 | .01 |
| Coherence length (L) in μm | 16 | 72 |

OPS 510 improves accuracy of the OV measurement without introducing interference between the sub-beams. OPS 510 may be used with broadband radiation regardless of whether the radiation is polarized or unpolarized.

FIG. 5 further depicts lenses L1 and L2 that form a double-telecentric system that images the illumination pupil 514 into the pupil plane PP of the high-NA (numerical aperture) lens L3. This objective lens L3 illuminates the target 503, which may be a small grating that is surrounded by an unknown product pattern. The input pupil aperture 506 is conjugate to the pupil aperture of the objective optical system and relay optics L1 and L2 form an intermediate image of the illumination source and relay the intermediate image to the objective optical system for imaging at the substrate. Lenses L1, L2 and L3 thus form an optical system that illuminates the target via the objective. The illumination spot on the wafer is normally chosen much larger than the grating. Typical values are, for example, a spot diameter of 30 μm projected on the wafer and grating size of 10×10 μm2. The embodiment will still work when the illumination spot is smaller than the grating, for example, with a relatively large grating in a scribe lane.

The illumination light that is scattered by the target grating 503 and the surrounding product area is collimated by lens L3 and the double telecentric system L3 and L4 make a magnified image of the grating and product environment on the field stop FS. The field stop FS is placed at the image plane formed by a relay consisting of the objective lens L3 and L4. The purpose of the field stop FS is to limit the spatial extent of the intermediate image and to suppress stray light in the detection optics. The spatial filter thus spatially filters radiation scattered from a surface of the substrate adjacent to the target to select radiation scattered by the target.

Lenses L4 and L5 re-image objective pupil plane PP onto an quadrature wedge QW. This image 526 of the pupil plane has four components of the light diffracted at substrate grating into 0, −1, 0' and +1' orders. Quadrature wedge QW redirects the light in the four quadrants of pupil plane 526 in four different directions. Thus quadrature wedge QW is an optical device configured to separately redirect diffraction orders of radiation scattered from the substrate. Quadrature wedge QW may comprise four wedges. As a result of quadrature wedge QW, lens L6 produces, in the image plane IP, four spatially separated sub images of the light that is transmitted by the field stop FS. As white light is used, quadrature wedge can be achromatic in order to reduce chromatic aberrations of wedges. Achromatic wedges can be made in transmission but reflective wedges are also suitable since they are intrinsically achromatic. The wedge angle is sufficiently large to allow a complete separation of the four sub images. If the separation is too small the images will overlap causing crosstalk from the product area into the grating area.

The four signals are measured for one given angle of incidence by a sensor 504 (e.g., a charge-coupled device). The skilled person will appreciate that this can be repeated for more angles of incidence by changing the location of the illumination spot in the illumination pupil plane. The set of measured spectra can now be used in processor unit PU to calculate asymmetry properties of the target grating. Asymmetry properties such as calculated overlay error (for a an overlay target with a stack of more than one superimposed grating) and asymmetry (for a single grating) can be determined by comparing the measured +1' and −1 spectra as in the Diffraction Based Overlay method.

Each of the OPS embodiments described herein may be utilized with the scatterometers described above. All OPS embodiments described herein induce an optical path difference (OPD) between sub-beams such that the first and second sub-beams have an OPD that is greater than a coherence length of the at least one beam and less than a depth of focus of the objective optical system. In addition, each OPS disclosed herein may be configured as a monolithic prism system formed of a plurality of adjoining prisms wherein an optical path of each sub-beam is substantially perpendicular (i.e., about 1 degree from perpendicular) to each prism surface at each interface. Thus, the input and output faces of OPS are tilted slightly to reduce ghost images. Further, each beam splitter of the OPS may be a non-polarizing beam splitter, e.g., a half-mirror. Though the embodiment disclosed generally show a single illumination beam path and two sub-beam paths, one or ordinary skill in the art will appreciate that multiple illumination beams may be used with these OPS examples.

FIG. 6 illustrates an example of how an OPS may be arranged utilizing a single beam splitter. OPS 610 includes a beam splitter 641 and two retroreflectors 630x, 630y. In one exemplary embodiment, beam splitter 641 may be a non-polarizing half-mirror that splits illumination beam 608 into two sub-beams, each being about 50% of the intensity of the incident illumination beam. Further, retroreflectors 630x, 630y may be Porro prisms arranged at adjacent sides of a beam splitting cube containing the non-polarizing half mirror. Each Porro prism reverses the incident beam about a respective x- or y-axis as it reflects the incident illumination beam back to the beam splitter 641. Thus, when the beams recombine, each has been revered about a different axis.

FIG. 7 illustrates an alternative arrangement of an OPS utilizing two beam splitters. OPS 710 includes a first beam splitter 741 to divide illumination beam 708 and a second beam splitter 745 to recombine the illumination sub-beams. In one exemplary embodiment, first beam splitter 741 may be a non-polarizing half-mirror that split illumination beam 708 into two sub-beams, each being about 50% of the intensity of the incident illumination beam. The portion of illumination beam 708 transmitted through first beam splitter 741 forms sub-beam 708a. Sub-beam 708a is directed through a first image rotator 732x that rotates sub-beam 708a about the x-axis. Sub-beam 708a is then reflected by fold mirror 744 toward second beam splitter 745. The portion of illumination beam 708 reflected by first beam splitter 741 forms sub-beam 708b. Sub-beam 708b is reflected by fold mirror 742 toward a second image rotator 732y that rotates sub-beam 708b about its y-axis. Sub-beam 708b is then output toward second beam splitter 745. Like first beam splitter 741, second beam splitter 745 may be a non-polarizing half-mirror that recombine illumination sub-beams. This arrangement results in two output beams (though only one is shown) each being about 50% of the intensity of the incident illumination beam.

The first and second image rotators may have a variety of configurations. Exemplary embodiments of the image rotators are detailed below. Further, the OPS 510, 610, 710 need not be made of physically separate components, but may be a single monolithic unit. Also, the direction of input and out beams is not limited to the embodiments disclosed as this is a matter of design choice. Notably, however, the exemplary embodiments of the OPS discussed below have been specifically designed such that the transmissive interface surfaces of the prisms are arranged to be substantially perpendicular to the optical axis (i.e., about 1 degree from perpendicular). The exemplary embodiments described here maximize transmission and minimize dispersion and flare.

Figure 8A:
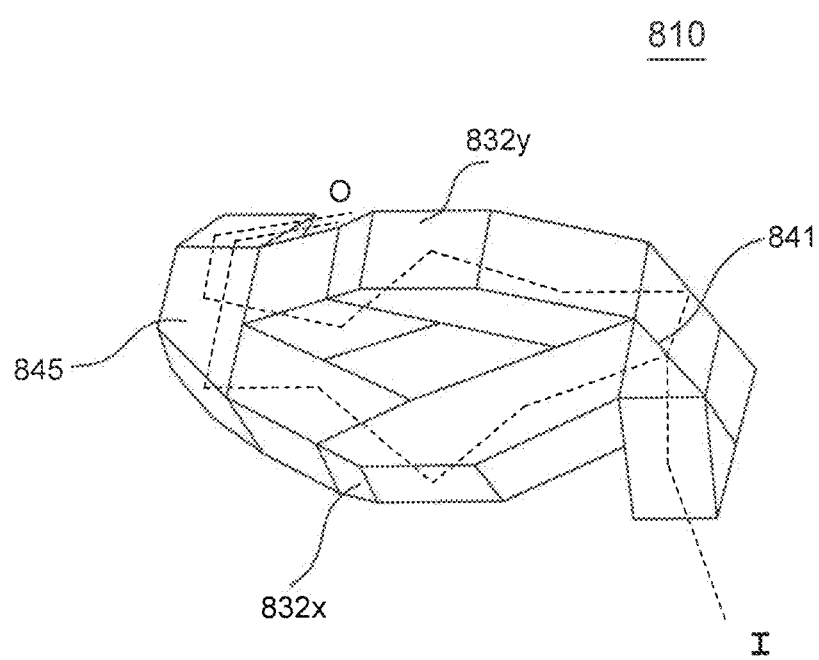
FIG. 8A illustrates a first exemplary monolithic prism system of the optical pupil symmetrizer with two beam splitters according to an exemplary embodiment.

FIG. 8A depicts a first exemplary monolithic prism system of the OPS 810 with two beam splitters 841, 845. Similar to OPS 710, OPS 810 includes beam splitters 841, 845 and image rotator systems 832x, 832y between the beam splitters. Image rotator systems 832x, 832y reflect the respective incident sub-beam three times, thereby rotating the images of the sub-beams by 180 degrees relative to each other. Further details of such image rotator systems 832x, 832y can be seen in FIGS. 9A and 9B.

Figure 8B:
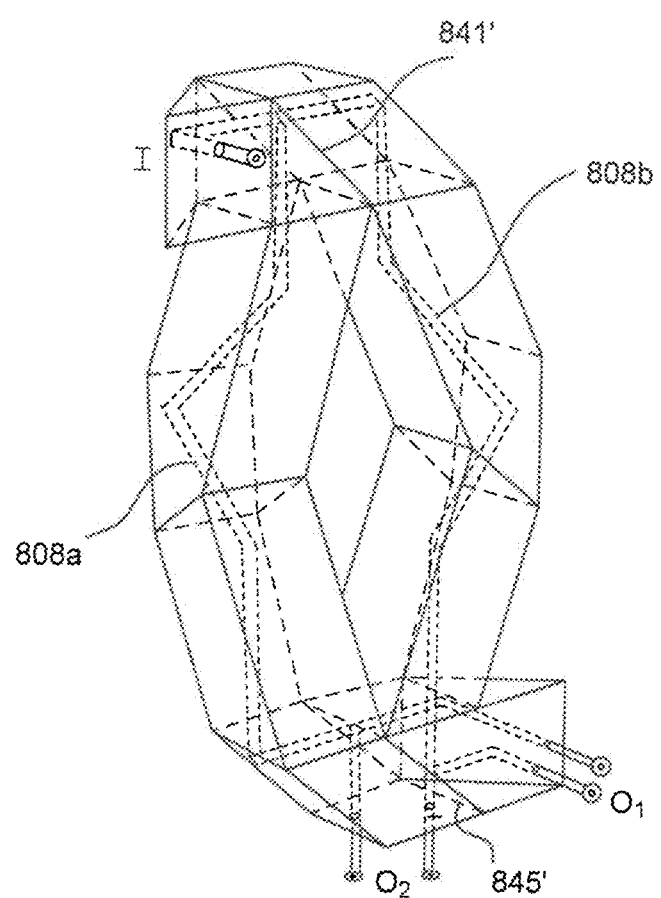
FIG. 8B illustrates a second exemplary monolithic prism system of the optical pupil symmetrizer with two beam splitters and two fold prisms according to an exemplary embodiment.

FIG. 8B depicts an exemplary embodiment a monolithic prism OPS 810. The monolithic prism 810 includes eight adjoined pieces, i.e., two fold prisms (reflecting by) 90°, two beam splitter prisms (including half-mirrors), and four internal reflecting wedge prisms (which form two image rotating systems). Thus, FIG. 8B is similar to FIG. 8A, but with a forty-five degree fold prism at the input I and output O1. A first fold prism reflects incident input illumination beam at a right angle to a first beam splitting prism. A portion of illumination beam (e.g., 50%) is then reflected by a first beam splitter 841' along a first branch to form a first sub-beam 808a. The remaining portion is transmitted through first beam splitter 841' along a second branch to form a second sub-beam 808b. First sub-beam 808a and second sub-beam 808b each enter image rotators that thrice reflect each sub-beam about substantially perpendicular axes. Beam splitter 845' recombines the sub-beams 808a, 808b before forming output O1. The prism system could alternatively or additionally be arranged to utilize output O2.

The OPS 810 illustrated has multiple prism optically joined together. Notably, the prism system is arranged such that the sub-beams encounter each interface substantially perpendicular to the incident surface. This arrangement minimizes chromatic aberrations that might be otherwise created.

Figure 9A:
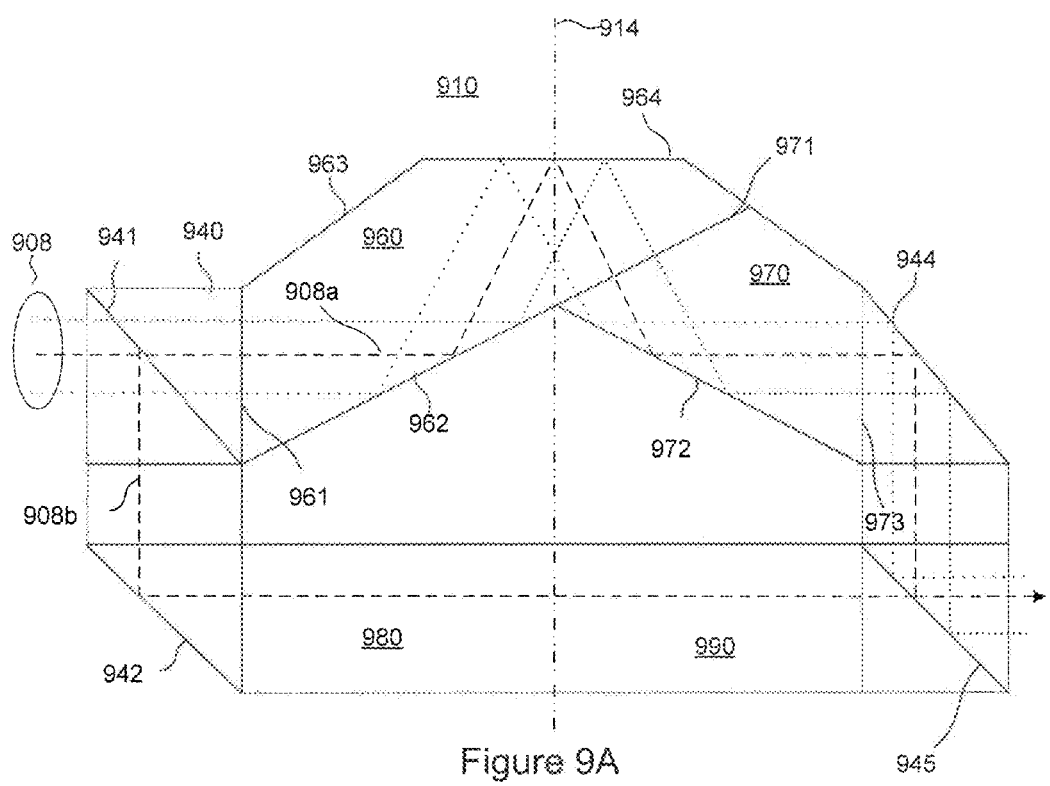
FIG. 9A shows a cross-sectional view of a third optical pupil symmetrizer system of the optical pupil symmetrizer with two beam splitters according to an exemplary embodiment.

As shown in side-view FIG. 9A, three different rays of beam 908, identified by three different dashed lines, trace a path of portions of a beam of light entering the prism system substantially perpendicular to a first planar surface of beam splitter prism 940. Beam splitter 941 divides incident beam 908 into sub-beams 908a, 908b. For simplicity, only rays of 908a are traced. But one of ordinary skill will appreciate that such rays might be similarly traced for sub-beam 908b. Sub-beam 908a enters a first reflecting prism 960 at surface 961. First reflecting prism 960 reflects sub-beam 908a at planar surface 962. Planar surface 962 is angled so that the rays of sub-beam 908a experience total internal reflection (TIR) at planar surface 962 and are reflected toward planar surface 964. Planar surface 964 reflects the rays of sub-beam 908a to planar surface 972. Surface 964 can be coated in order to increase reflectance from it if beam angle of incidence is less than the critical angle needed for total internal reflection. Planar surface 972 is angled so that the rays of sub-beam 908a again experience TIR and emerge from second reflecting prism 970 substantially perpendicular to planar surface 973. Because the rays of sub-beam 908a experience an odd number of reflections, of sub-beam 908a emerges from second reflecting prism 970 inverted with respect to the incident orientation of the rays of sub-beam 908a.

Figure 9B:
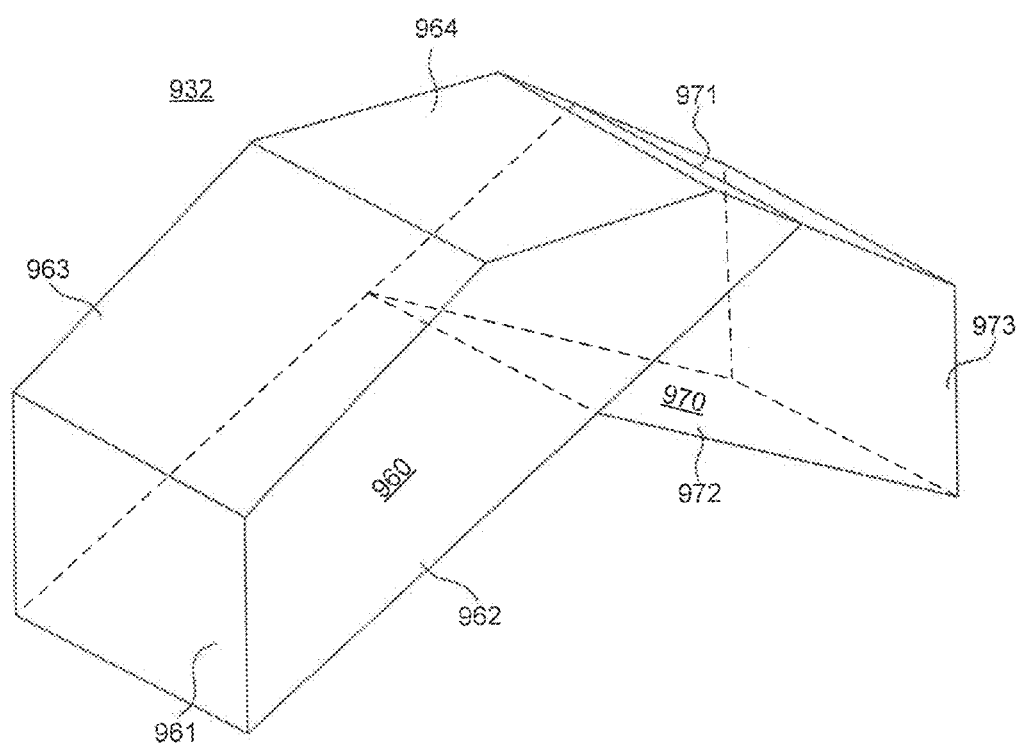
FIG. 9B depicts an angled view of an image rotator of the prism configuration of FIG. 9A according to an exemplary embodiment.

Sub-beam 908b follows a similar path through first reflecting prism 980 and second reflecting prism 990. The two sub-beams 908a and 908b converge at a second beam splitter 945. FIG. 9B illustrates and angled view of the first and second reflecting prisms 960, 970.

Figure 10:
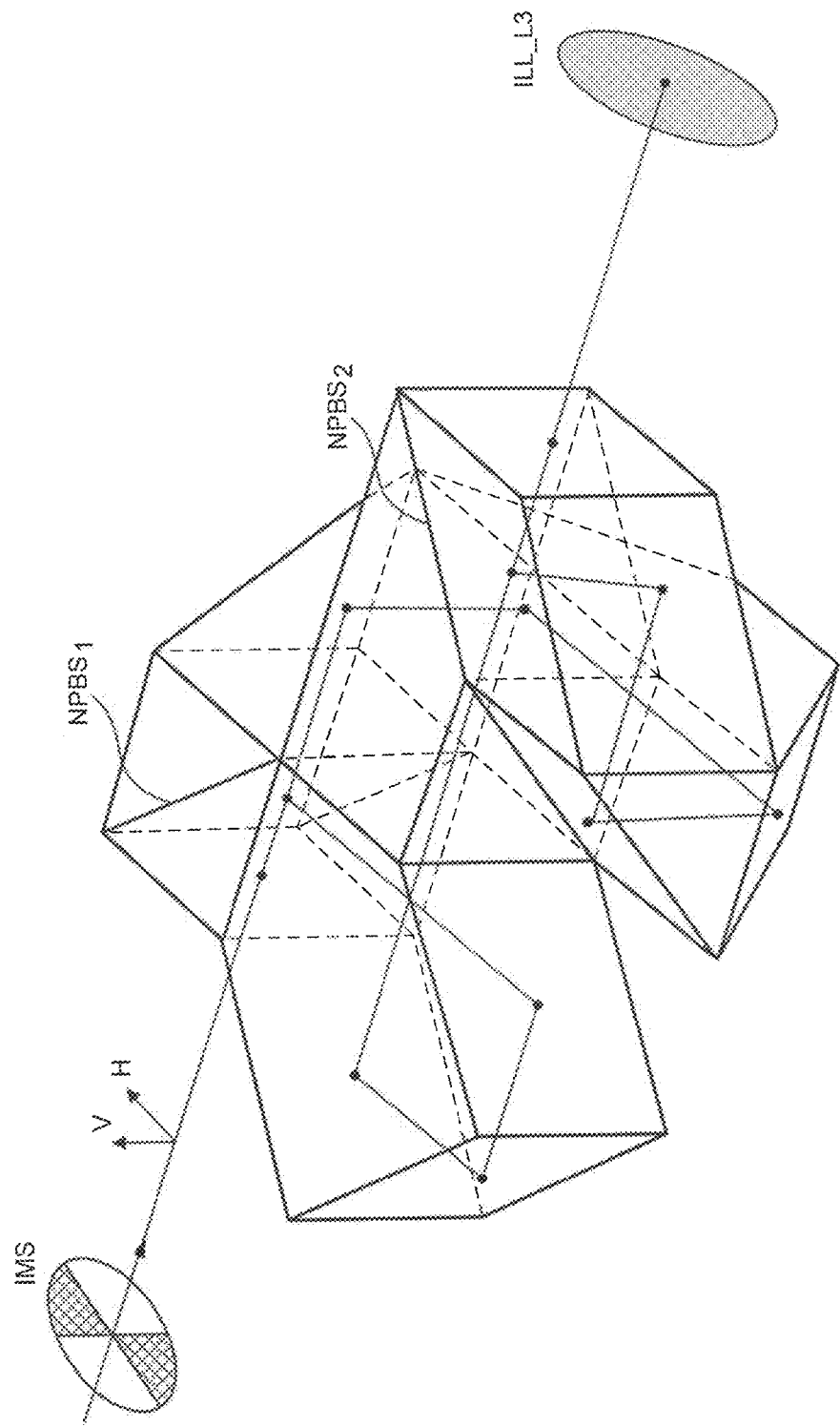
FIG. 10 depicts a third exemplary monolithic prism system of the optical pupil symmetrizer with two beam splitters according to an exemplary embodiment.

In another exemplary embodiment, the OPS FIG. 10 depicts a third exemplary monolithic prism system of the optical pupil symmetrizer with two beam splitters.

Figure 11:
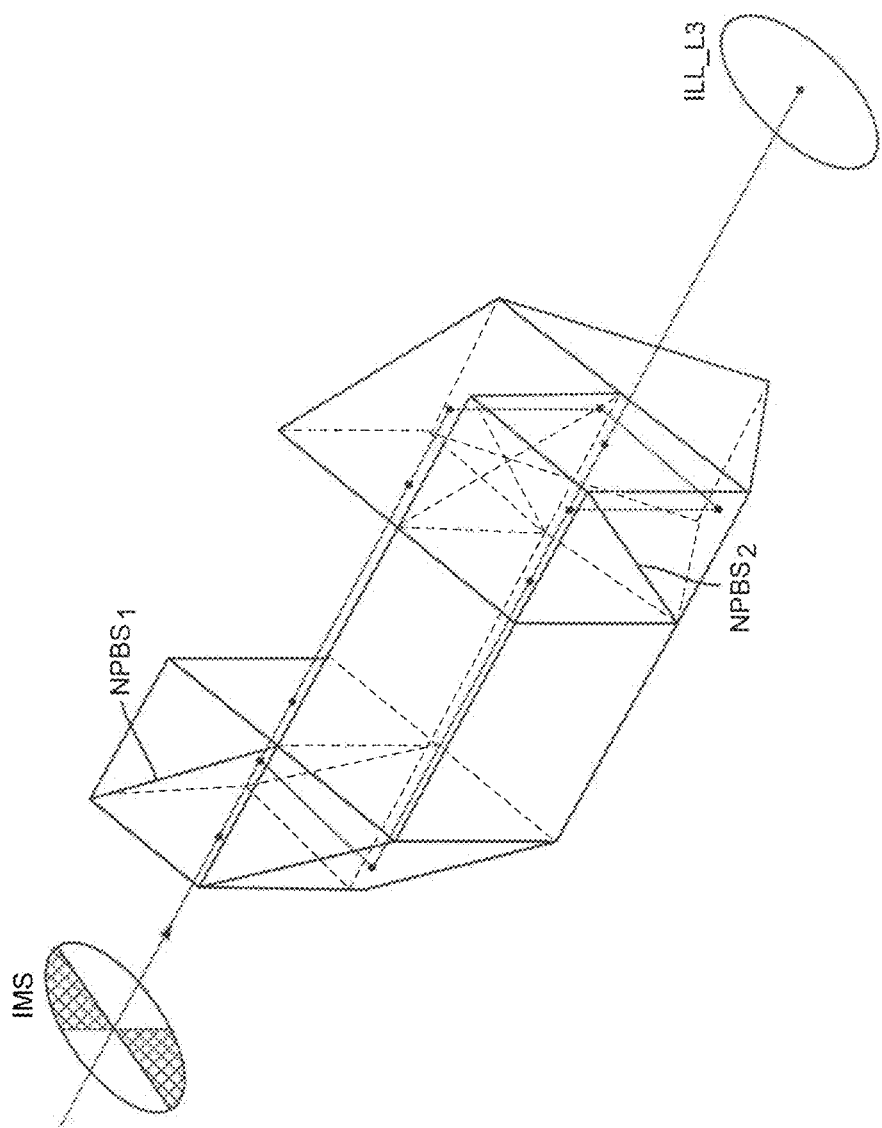
FIG. 11 depicts a fourth exemplary monolithic prism system of the optical pupil symmetrizer with two beam splitters according to an exemplary embodiment.

In yet another exemplary embodiment, the OPS may include a modified Porro-Abbe prism system. As shown in FIG. 11 the illumination beam is split by a non-polarizing beam splitter NPBS1. The transmitted sub-beam enters a modified Porro-Abbe prism, which functions as an image rotator. The modified Porro-Abbe prism differs from a conventional Porro-Abbe prism because a second non-polarizing beam splitter NPBS2 replaces the last reflective surface.

The portion of the illumination beam reflected by the first non-polarizing beam splitter NPBS1 forms a reflected sub-beam. The reflected sub-beam is, in turn, reflected by a fold prism toward the Porro-Abbe prism. After passing through an optical slab, the two sub-beams are recombined by the second beam splitting cube. The output beam is parallel, but "horizontally" shifted, compared to the input beam. (The term "horizontally" is intended to reflect a natural orientation of the figure shown and not an orientation within an actual implementation.)

Figure 12A:
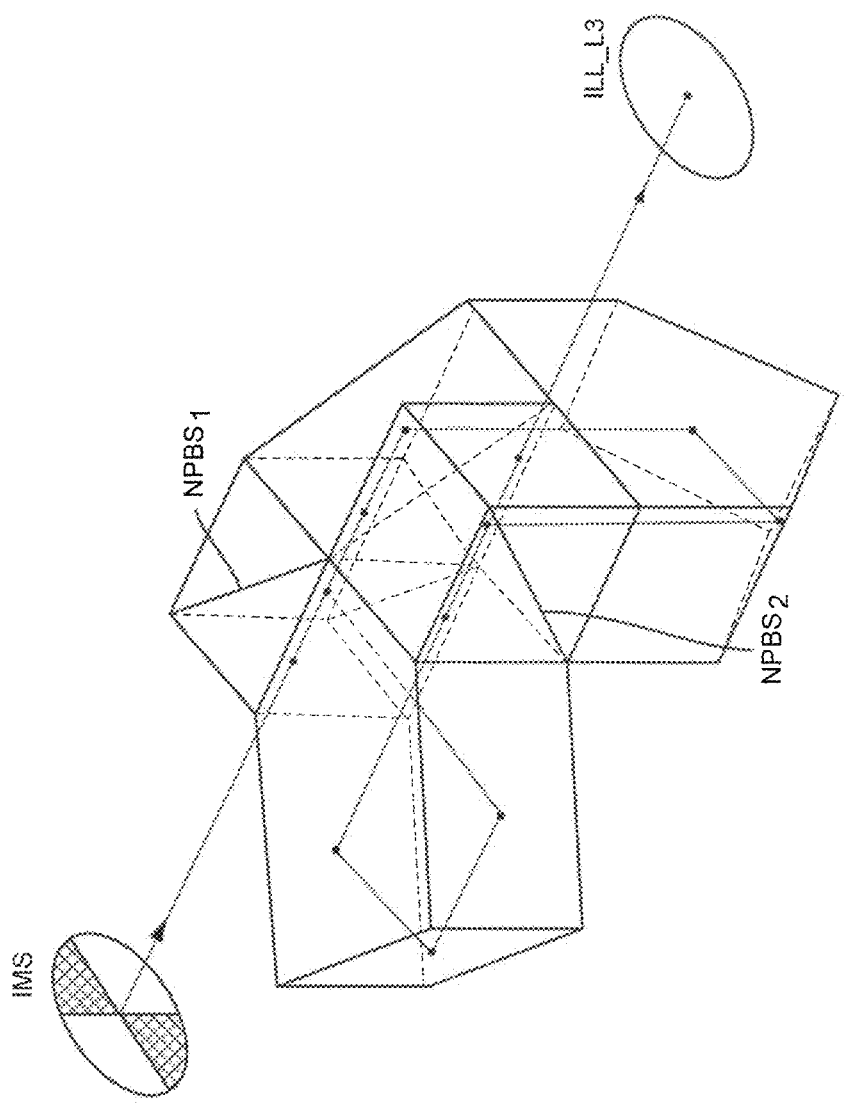
FIG. 12A depicts a fifth exemplary monolithic prism system of the optical pupil symmetrizer with two beam splitters according to an exemplary embodiment.

In a modified version of the exemplary embodiment illustrated FIG. 11, the OPS may have a thrice-reflecting Porro prism instead of the fold prism and optical slab. As depicted in FIG. 12A, after splitting the illumination, the reflected portion of the illumination beam enters one side of a seven-sided Porro prism. The sub-beam is then reflected three times by three adjacent sides before exiting, thereby rotating an image of the reflected sub-beam. The reflected sub-beam is the recombined with the transmitted sub-beam that was rotated by a modified Porro-Abbe prism as discussed above with respect to FIG. 11.

Figure 12B:
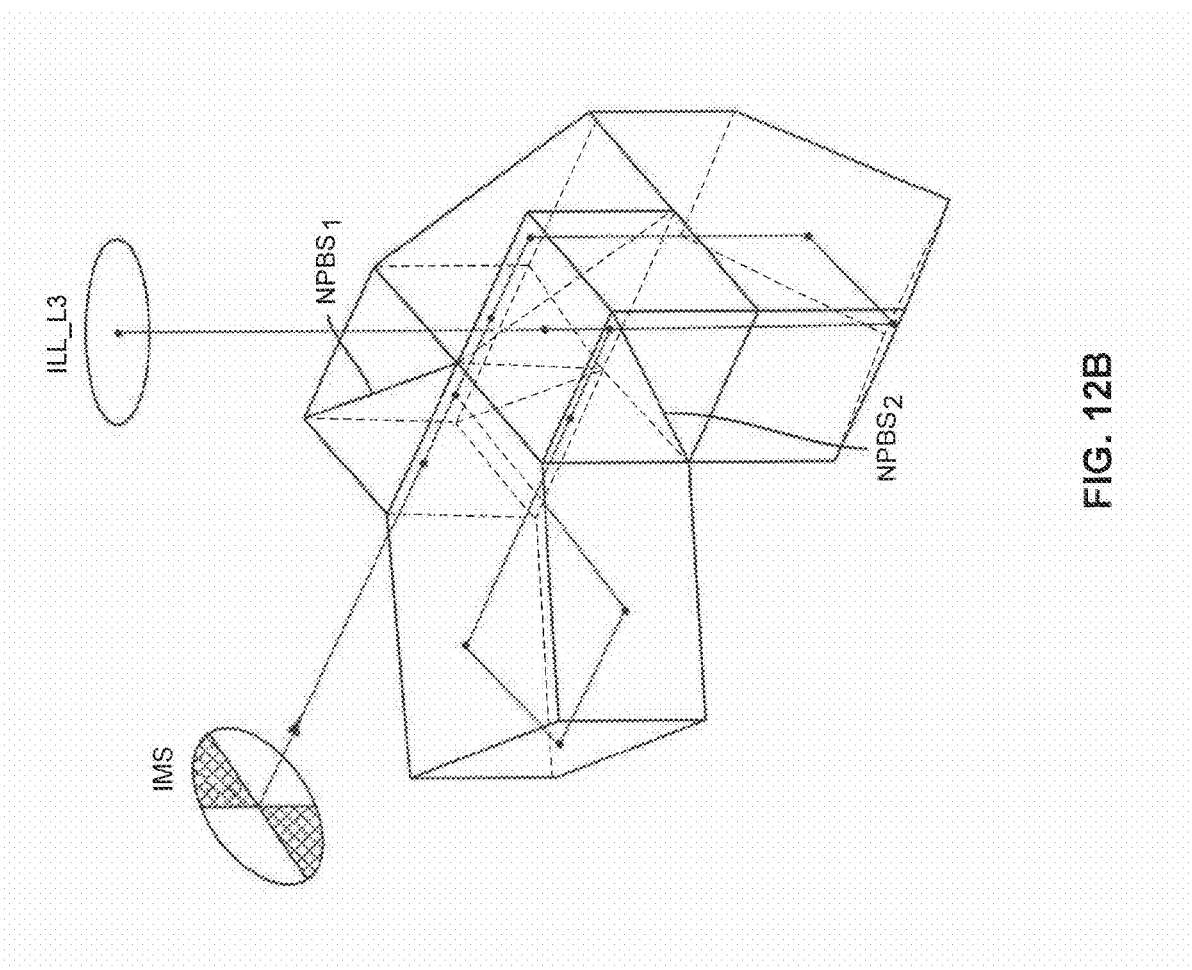
FIG. 12B depicts a first variation of the fifth exemplary monolithic prism system of the optical pupil symmetrizer with two beam splitters according to an exemplary embodiment.

FIG. 12B depicts a first variation of the exemplary embodiment of optical pupil symmetrizer illustrated in FIG. 12A. The embodiment of FIG. 12B differs from the embodiment of FIG. 12A in that optical axis of the output beam is substantially perpendicular to the input beam.

Figure 12C:
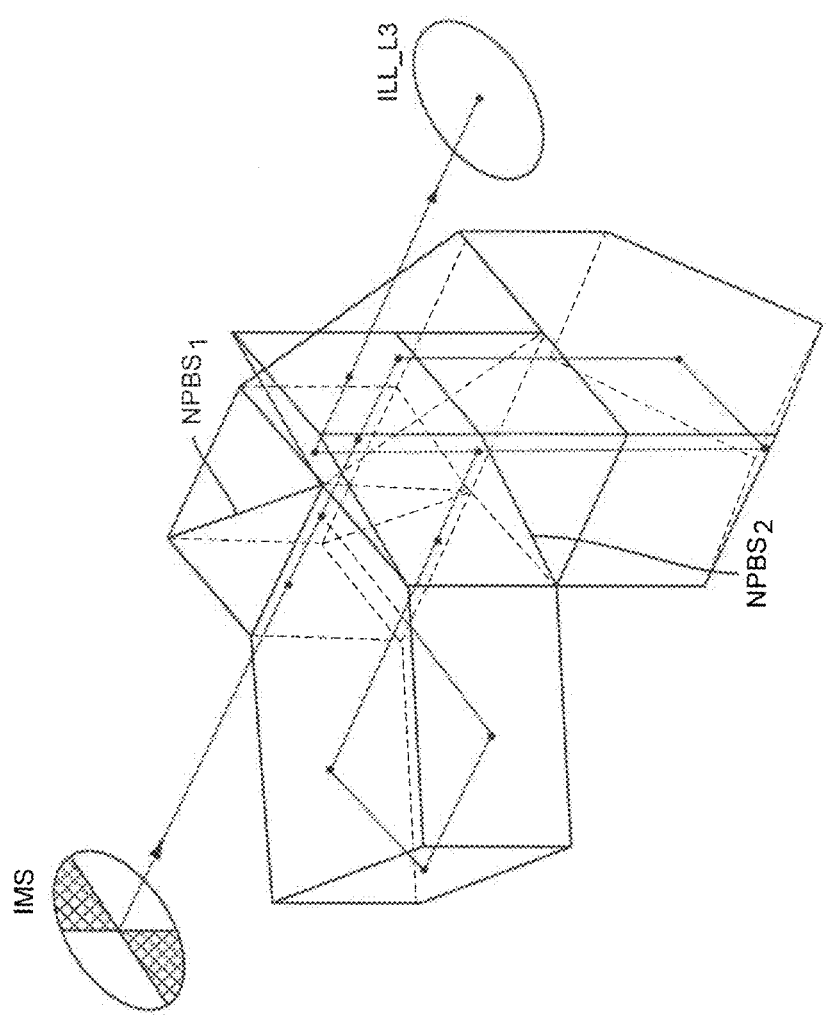
FIG. 12C depicts a second variation of the fifth exemplary monolithic prism system of the optical pupil symmetrizer with two beam splitters according to an exemplary embodiment.

FIG. 12C depicts a second variation of the exemplary embodiment of optical pupil symmetrizer illustrated in FIG. 12A. Like the embodiment of FIG. 12A the output beam is parallel to the input beam. The output beam of FIG. 12C, however, is both vertically and horizontally shifted. A rhomboidal prism is integrated into the second beam splitter cube to accomplish this vertical shift.

Figure 13:
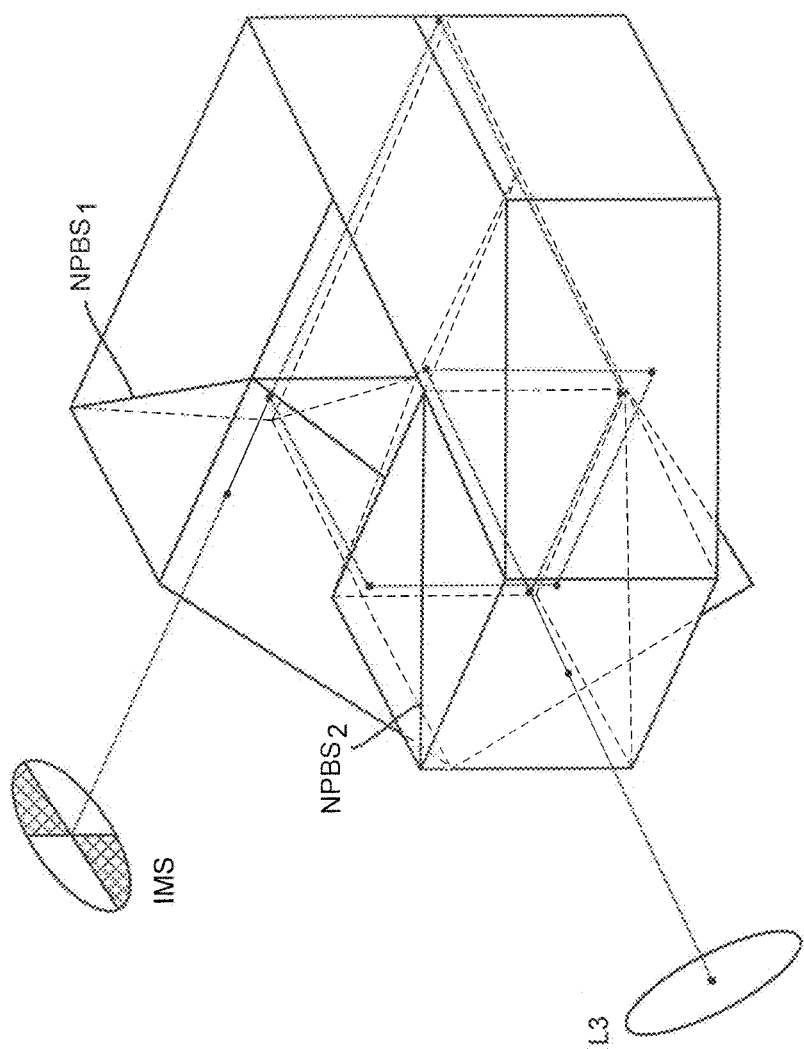
FIG. 13 depicts a sixth exemplary monolithic prism system of the optical pupil symmetrizer with two beam splitters according to an exemplary embodiment.

In still another exemplary embodiment, another modified Porro-Abbe prism may be used to rotate a portion of the illumination beam. As depicted in FIG. 13, a first non-polarizing beam splitter NPBS1 may divide the illumination beam into a reflected sub-beam and a transmitted sub-beam. The reflected sub-beam is directed through a Porro-Abbe prism before entering a second non-polarizing beam splitter NPBS2. The transmitted sub-beam is directed to a truncated Porro prism or Dove prism, which twice reflects the transmitted sub-beam before reaching the second non-polarizing beam splitter NPBS2. The sub-beams may then be recombined as discussed above.

Figure 14:
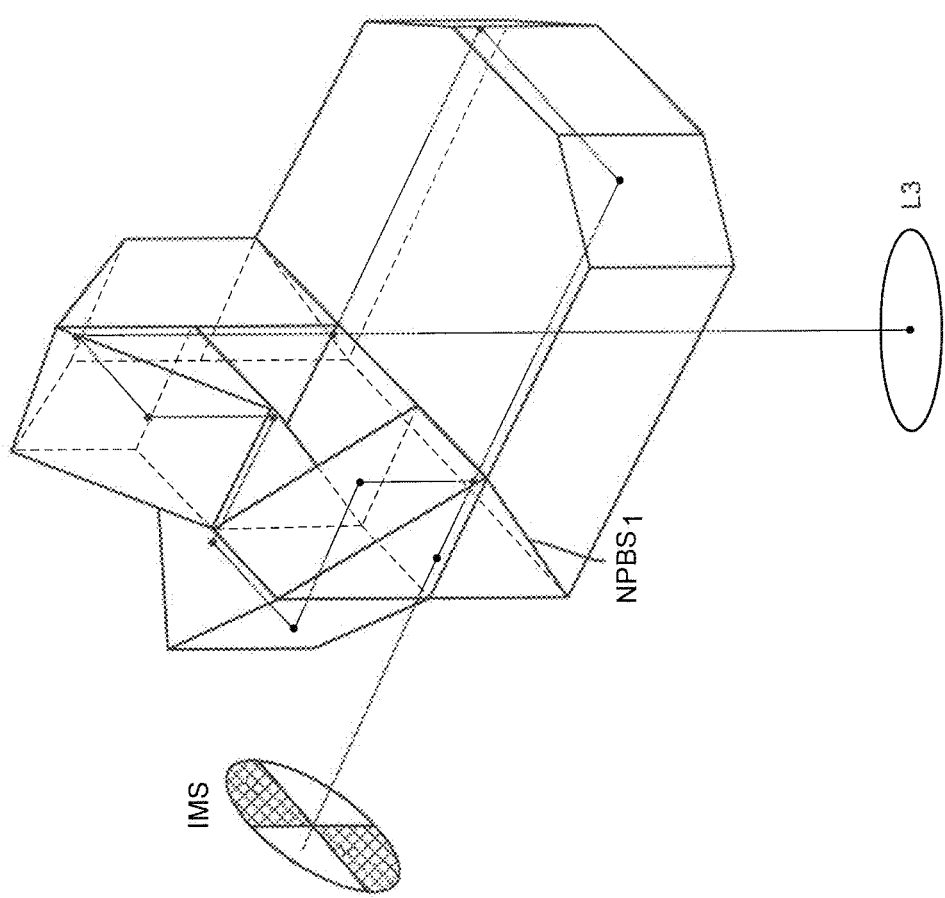
FIG. 14 depicts a seventh exemplary monolithic prism system of the optical pupil symmetrizer with a single beam splitter according to an exemplary embodiment.
Figure 15A:
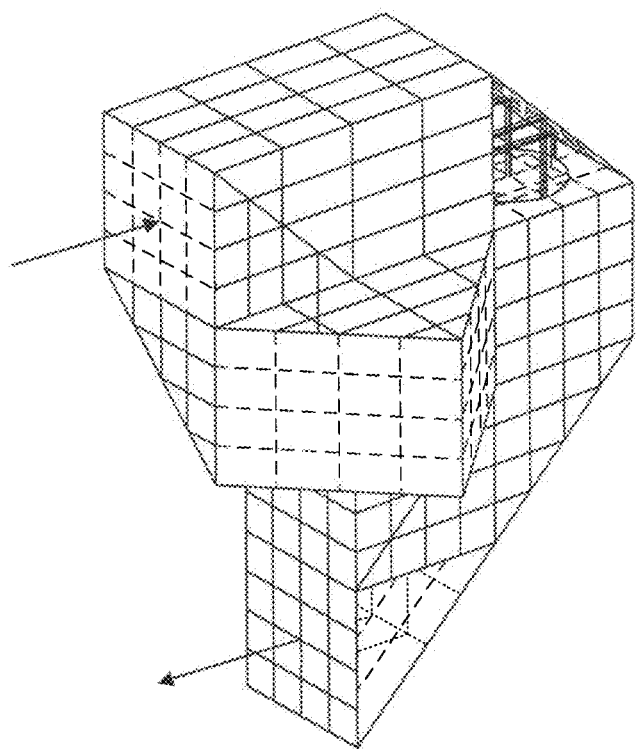
FIGS. 15A-15F depicts a eighth exemplary monolithic prism system of the optical pupil symmetrizer with two beam splitters according to an exemplary embodiment.
Figure 15B:
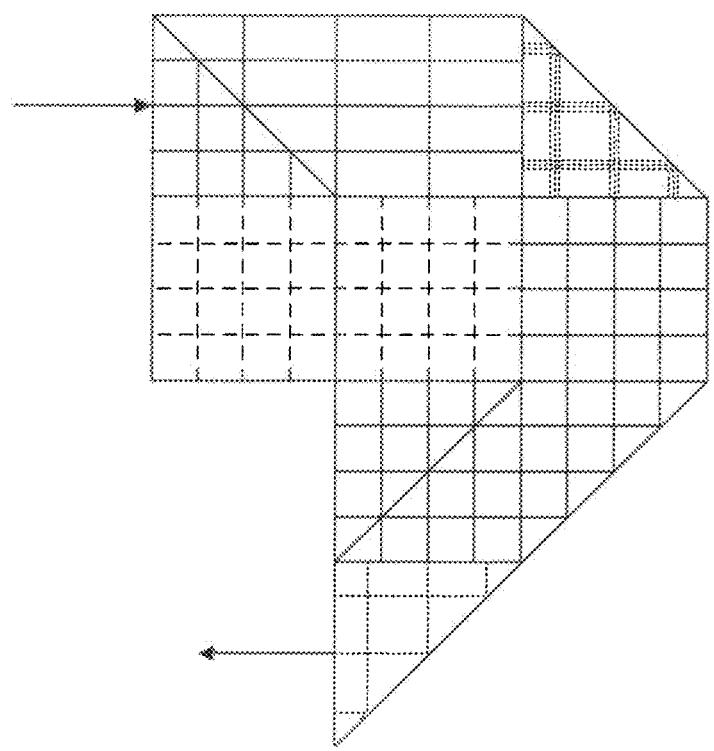
Figure 15C:
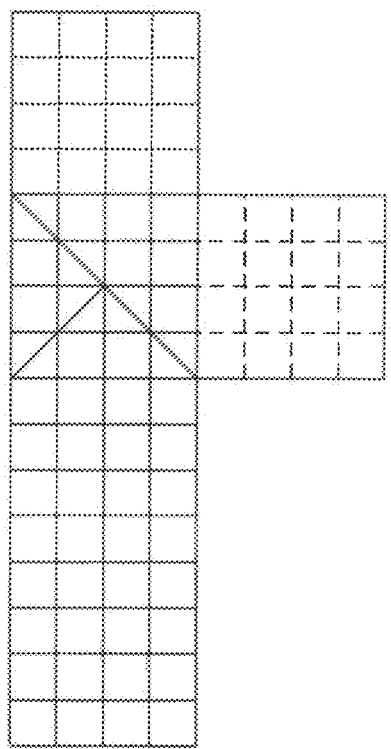
Figure 15D:
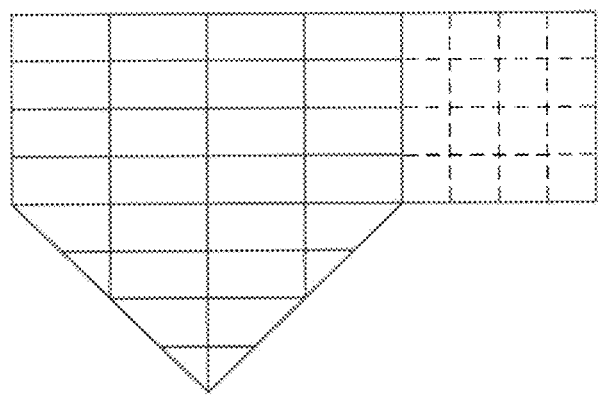
Figure 15E:
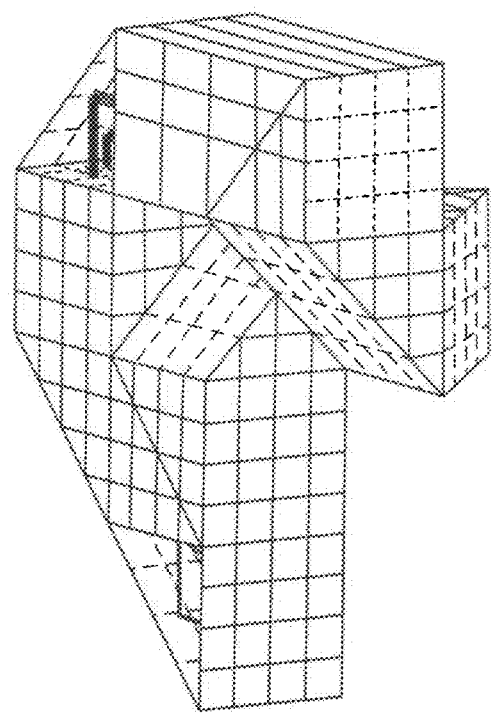
Figure 15F:
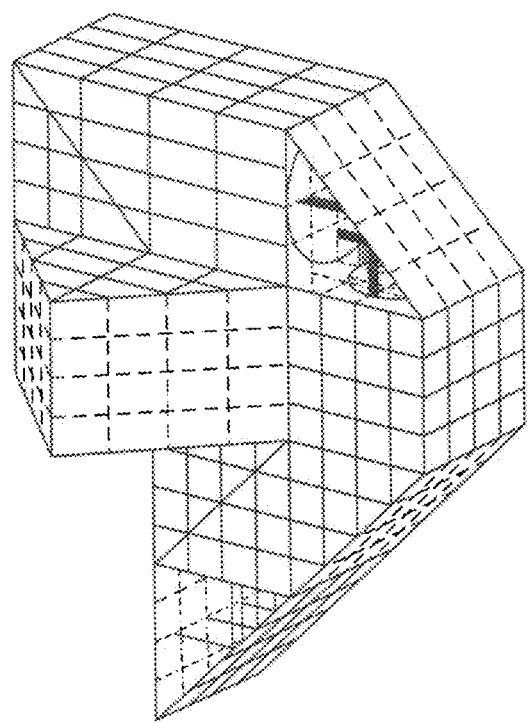

In another exemplary embodiment, a single non-polarizing beam splitter NPBS1 is used to both split and recombine the illumination beam. As shown in FIG. 14, non-polarizing beam splitter NPBS1 divides the illumination beam into transmitted and reflected sub-beams. The transmitted sub-beam is internally reflected by two angled sides of the beam splitter prism. The transmitted sub-beam is then reflected by non-polarizing beam splitter NPBS1 towards lens L3. The reflected sub-beam is reflected in series by a first fold prism (reflecting by 90°), a Porro prism (reflecting twice by 90°), a second fold prism, a third fold prism (reflecting by 90°), and a fourth prism (reflecting by 90°). After these reflections, the portion of the illumination beam reflected by non-polarizing beam splitter NPBS1 may then be transmitted through non-polarizing beam splitter NPBS1, thereby recombining with at least a portion of the sub-beam originally transmitted by non-polarizing beam splitter NPBS1.

In final exemplary embodiment, simplified prism structures are arranged to split, rotate, and recombine the illumination beam. This exemplary embodiment alleviates the use of more complicated prism structures or angles of reflection. FIGS. 15A-15F illustrate the exemplary optical pupil symmetrizer using two-beam splitters and a plurality of right fold prisms for right angle reflections. Non-polarizing beam splitter NPBS1 (e.g., at 45° with respect to the input illumination beam I) divides the illumination beam into transmitted and reflected sub-beams. The reflected sub-beam enters a series of four fold prisms that invert the reflected sub-beam before recombination with transmitted sub-beam. The series of four fold prisms may be, for example, an Porro-Abbe prism. The reflected sub-beam is reflected four times internally and emitted parallel, but laterally offset relative to the normal incidence on the Porro-Abbe prism. This results in minimal dispersion.

The transmitted sub-beam is twice reflected by fold prism before recombination with the reflected sub-beam by non-polarizing beam splitter NPBS2. In the embodiment shown, the reflected sub-beam from non-polarizing beam splitter NPBS1 is transmitted by non-polarizing beam splitter NPBS2 and the transmitted sub-beam from non-polarizing beam splitter NPBS1 is reflected by non-polarizing beam splitter NPBS2 to form an output beam O. A final fold prism (reflecting by 90°) may be used reflect the recombined sub-beams such that the output beam O is parallel to the input beam I.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams. As mentioned above, the term radiation in the context of the driving system may also encompass microwave radiation.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

What we claim is:

1. An scatterometer for overlay measurement, the scatterometer comprising:

an illumination system configured to deliver at least one beam of radiation;

an objective optical system configured to focus the at least one beam onto the substrate, the objective optical system having a pupil aperture; and a detection system configured to detect light reflected from the substrate;

wherein the illumination system comprises an optical pupil symmetrization (OPS) system configured to symmetrize the at least one beam at a pupil plane of the objective optical system, the OPS system comprising:

at least one beam splitter configured to split the at least one beam into a first sub-beam and a second sub-beam and recombine the first and second sub-beams; and at least two optical branches configured to (i) respectively receive and reflect the first and second sub-beams, (ii) rotate at least the second sub-beam such that an intensity distribution of the second sub-beam is inverted, and (iii) recombine the first sub-beam with the second sub-beam such that the second sub-beam is symmetric relative to the first sub-beam;

wherein the OPS system is further configured such that the first and second sub-beams have an optical path difference that is greater than a temporal coherence length of the at least one beam and less than a depth of focus in the pupil plane of the objective optical system.

2. The scatterometer of claim 1, wherein the optical path difference is in a range of about 50 µm to about 100 µm.

3. The scatterometer of claim 1, wherein the illumination system further comprises at least one light source and an input pupil aperture that is conjugate to the pupil aperture of the objective optical system and relay optics that form an intermediate image of the at least one light source and relay the intermediate image to the objective optical system for imaging at the substrate.

4. The scatterometer of claim 3, wherein the input pupil aperture of the illumination system comprises a spatial filter configured to block light in at least two of four quadrants of the input pupil aperture of the illumination system.

5. The scatterometer of claim 1, wherein the illumination system further comprises at least one light source, the light source comprising:

a broadband light source configured to emit light in the range of 400 nm to 905 nm; and a tunable filter configured to transmit a narrow band of light which has a width of 10 nm to 40 nm of the emitted light and block remaining emitted light.

6. The scatterometer of claim 1, wherein the OPS system is configured to rotate the second sub-beam such that the first and second sub-beams are rotated 180° about an optical axis with respect to each other.

7. The scatterometer of claim 6, wherein the OPS system is further configured to rotate the first and second sub-beams such that the first and second sub-beams are each rotated 90° about an optical axis.

8. The scatterometer of claim 1, wherein the OPS system is a monolithic module.

9. The scatterometer of claim 1, wherein the at least one beam splitter is a non-polarizing beam splitter.

10. The scatterometer of claim 1, wherein the OPS system comprises a plurality of adjoining prisms and an optical path of each sub-beam is substantially perpendicular to each prism surface at each interface.

11. The scatterometer of claim 1, wherein the at least two optical branches comprise at least one image-rotating optical system for each branch.

12. The scatterometer of claim 11, wherein the OPS system further comprises:
   a first beam splitter prism configured to split the at least one beam into the first sub-beam and the second sub-beam;
   a first image-rotating prism system configured to thrice reflect the first sub-beam;
   a second image-rotating prism system configured to thrice reflect the second sub-beam; and
   a second beam splitter prism to recombine the first and second sub-beams.

13. The scatterometer of claim 11, wherein the first and second image-rotating optical systems each comprise a seven-sided prism, each seven-sided prism having a side adjoining the first or second beam splitter prism.

14. The scatterometer of claim 11, wherein the first and second image-rotating prism systems each comprise two wedge prisms configured to reflect the first or second sub-beam at least twice by total internal reflection.

15. A lithographic apparatus comprising:
   a first illumination optical system configured to illuminate a pattern;
   a projection optical system arranged to project an image of the pattern onto a substrate;
   a scatterometer configured to determine a focus of the lithographic apparatus, the scatterometer comprising:
      an illumination optical system configured to deliver at least one beam of radiation;
      an objective optical system configured to focus the at least one beam onto the substrate, the objective optical system having a pupil aperture; and
      a detection system configured to detect light reflected from the substrate;
      wherein the illumination optical system comprises an optical pupil symmetrization (OPS) system configured to symmetrize the at least one beam at a pupil plane of the objective optical system, the OPS system comprising:
         at least one beam splitter configured to split the at least one beam into a first sub-beam and a second sub-beam and recombine the first and second sub-beams; and
         at least two optical branches configured to (i) respectively receive and reflect the first and second sub-beams, (ii) rotate at least the second sub-beam such that an intensity distribution of the second sub-beam is inverted, and (iii) recombine the first sub-beam with the second sub-beam such that the second sub-beam is symmetric relative to the first sub-beam;
         wherein the OPS system is further configured such that the first and second sub-beams have an optical path difference that is greater than a temporal coherence length of the at least one beam and less than a depth of focus in the pupil plane of the objective optical system.

16. The lithographic apparatus of claim 15, wherein the optical path difference is in the range of about 50 μm to about 100 μm.

17. The lithographic apparatus of claim 15, wherein the illumination system further comprises at least one light source and an input pupil aperture that is conjugate to the pupil aperture of the objective optical system and relay optics that form an intermediate image of the at least one light source and relay the intermediate image to the objective optical system for imaging at the substrate.

18. The lithographic apparatus of claim 17, wherein the input pupil aperture of the illumination system comprises a spatial filter configured to block light in at least two of four quadrants of the input pupil aperture of the illumination system.

19. The lithographic apparatus of claim 15, wherein the illumination system further comprises at least one light source, the light source comprising:
   a broadband light source configured to emit light in the range of 400 nm to 905 nm; and
   a tunable filter configured to transmit a narrow band of light which has a width of 10 nm to 40 nm of the emitted light and block remaining emitted light.

20. The lithographic apparatus of claim 15, wherein the OPS system is configured to rotate the second sub-beam such that the first and second sub-beams are rotated 180° about an optical axis with respect to each other.

21. The lithographic apparatus of claim 15, wherein the OPS system is further configured to rotate the first and second sub-beams such that the first and second sub-beams are each rotated 90° about an optical axis.

22. The lithographic apparatus of claim 15, wherein the OPS system is a monolithic module.

23. The lithographic apparatus of claim 15, wherein the at least one beam splitter is a non-polarizing beam splitter.

24. The lithographic apparatus of claim 15, wherein the OPS system comprises a plurality of adjoining prisms and an optical path of each sub-beam is substantially perpendicular to each prism surface at each interface.

25. The lithographic apparatus of claim 15, wherein the at least two optical branches comprise at least one image-rotating optical system for each branch.

26. The lithographic apparatus of claim 15, wherein the OPS system further comprises:
   a first beam splitter prism configured to split the at least one beam into the first sub-beam and the second sub-beam;
   a first image-rotating prism system configured to thrice reflect the first sub-beam;
   a second image-rotating prism system configured to thrice reflect the second sub-beam; and
   a second beam splitter prism to recombine the first and second sub-beams.

27. The lithographic apparatus of claim 26, wherein the first and second image-rotating optical systems each comprise a seven-sided prism, each seven-sided prism having a side adjoining the first or second beam splitter prism.

28. The lithographic apparatus of claim 26, wherein the first and second image-rotating prism systems each comprise two wedge prisms configured to reflect the first or second sub-beam at least twice by total internal reflection.

29. A method for symmetrizing a pupil plane image:
   illuminating a substrate with at least one beam of radiation;
   focusing the at least one beam onto the substrate via an objective optical system, the objective optical system having a pupil aperture;
   detecting the at least one beam reflected from the substrate;
   wherein the illuminating comprises symmetrizing the at least one beam at a pupil plane of the objective optical system using an optical pupil symmetrization (OPS) system by:

splitting the at least one beam into a first sub-beam and second sub-beam and recombining the first and second sub-beams;

respectively receiving and reflecting the first and second sub-beams along at least two optical branches;

rotating at least the second sub-beam such that an intensity distribution of the second sub-beam is inverted; and recombining the first sub-beam with the second sub-beam such that the second sub-beam is symmetric relative to the first sub-beam;

wherein symmetrizing first and second sub-beams creates an optical path difference that is greater than a temporal coherence length of the at least one beam light source and less than a depth of focus in the pupil plane of the objective optical system.

30. A monolithic prism system comprising:

at least one beam splitter configured to split at least one beam into a first sub-beam and a second sub-beam and recombine the first and second sub-beams; and at least two optical branches configured to (i) respectively receive and reflect the first and second sub-beams, (ii) rotate at least the second sub-beam such that an intensity distribution of the second sub-beam is inverted, and (iii) recombine the first sub-beam with the second sub-beam such that the second sub-beam is symmetric relative to the first sub-beam;

wherein the monolithic prism system is further configured such that the first and second sub-beams have an optical path difference that is greater than a temporal coherence length of the at least one beam and less than a depth of focus in a pupil plane of an objective optical system.

* * * * *

UNITED STATES PATENT AND TRADEMARK OFFICE
CERTIFICATE OF CORRECTION

PATENT NO. : 9,904,173 B2
APPLICATION NO. : 14/970247
DATED : February 27, 2018
INVENTOR(S) : Shmarev et al.

Page 1 of 1

It is certified that error appears in the above-identified patent and that said Letters Patent is hereby corrected as shown below:

In the Claims

In Claim 15, Column 17, Line 27, after "substrate;" please enter "and".

In Claim 29, Column 19, Line 15, please delete "light source".

Signed and Sealed this
Twenty-first Day of August, 2018

Andrei Iancu
*Director of the United States Patent and Trademark Office*